US009393019B2

(12) United States Patent
Matonick et al.

(10) Patent No.: US 9,393,019 B2
(45) Date of Patent: Jul. 19, 2016

(54) THERAPY DELIVERY DEVICE FOR ANASTOMOTIC JOINING OF TISSUE

(71) Applicant: Ethicon, Inc., Somerville, NJ (US)

(72) Inventors: John Matonick, Warren, NJ (US); Leo B. Kriksunov, Ithaca, NY (US); Robert J. Tannhauser, Bridgewater, NJ (US)

(73) Assignee: Ethicon, Inc., Somerville, NJ (US)

( * ) Notice: Subject to any disclaimer, the term of this patent is extended or adjusted under 35 U.S.C. 154(b) by 469 days.

(21) Appl. No.: 14/068,282

(22) Filed: Oct. 31, 2013

(65) Prior Publication Data

US 2015/0115014 A1    Apr. 30, 2015

(51) Int. Cl.
*A61B 17/115*    (2006.01)
*A61B 17/00*    (2006.01)
*A61B 17/11*    (2006.01)
*A61M 37/00*    (2006.01)

(52) U.S. Cl.
CPC ....... *A61B 17/1155* (2013.01); *A61B 17/00491* (2013.01); *A61B 2017/00876* (2013.01); *A61B 2017/00884* (2013.01); *A61B 2017/00893* (2013.01); *A61B 2017/1132* (2013.01); *A61M 2037/003* (2013.01); *A61M 2037/0023* (2013.01); *A61M 2037/0061* (2013.01)

(58) Field of Classification Search
CPC .................................................. A61B 17/1155
USPC ..................... 227/19, 175.1, 176.1
See application file for complete search history.

(56) References Cited

U.S. PATENT DOCUMENTS

| 5,271,544 | A | 12/1993 | Fox et al. |
| 7,744,624 | B2 | 6/2010 | Bettuchi |
| 7,845,536 | B2 * | 12/2010 | Viola ............... A61B 17/00491 |
| | | | 227/175.1 |
| 8,096,458 | B2 | 1/2012 | Hessler |
| 8,241,308 | B2 | 8/2012 | Kortenbach et al. |
| 8,281,975 | B2 | 10/2012 | Criscuolo et al. |
| 2005/0184121 | A1* | 8/2005 | Heinrich ............ A61B 17/0686 |
| | | | 227/175.1 |
| 2006/0108393 | A1 | 5/2006 | Heinrich et al. |
| 2007/0038181 | A1 | 2/2007 | Melamud et al. |
| 2011/0014181 | A1 | 1/2011 | Thornton |
| 2011/0147432 | A1 | 6/2011 | Heinrich et al. |
| 2013/0068819 | A1 | 3/2013 | Viola |

OTHER PUBLICATIONS

Jonsson, K., et al. "Breaking Strength of Small Intestine Anastomoses", Am J Surg., pp. 800-803, 1983.
Yik-Hong, Ho, et al. "Techniques for Colorectal Anastomosis", World Journal of Gasteroenterology, pp. 1610-1621, 2010.
US 8,152,042, 04/2012, Bettuchi et al. (withdrawn)

* cited by examiner

*Primary Examiner* — Nathaniel Chukwurah
(74) *Attorney, Agent, or Firm* — David R. Crichton

(57) ABSTRACT

The present invention relates to circular anastomosis stapler kits that deliver a therapeutic agent followed by stapling of tissue. Each device has a stapling head with a shaft extending from said stapling head and a removable anvil and an interchangeable delivery head for delivering a therapeutic agent into the tissue. The present invention also relates to methods for using the kits and devices therein.

20 Claims, 16 Drawing Sheets

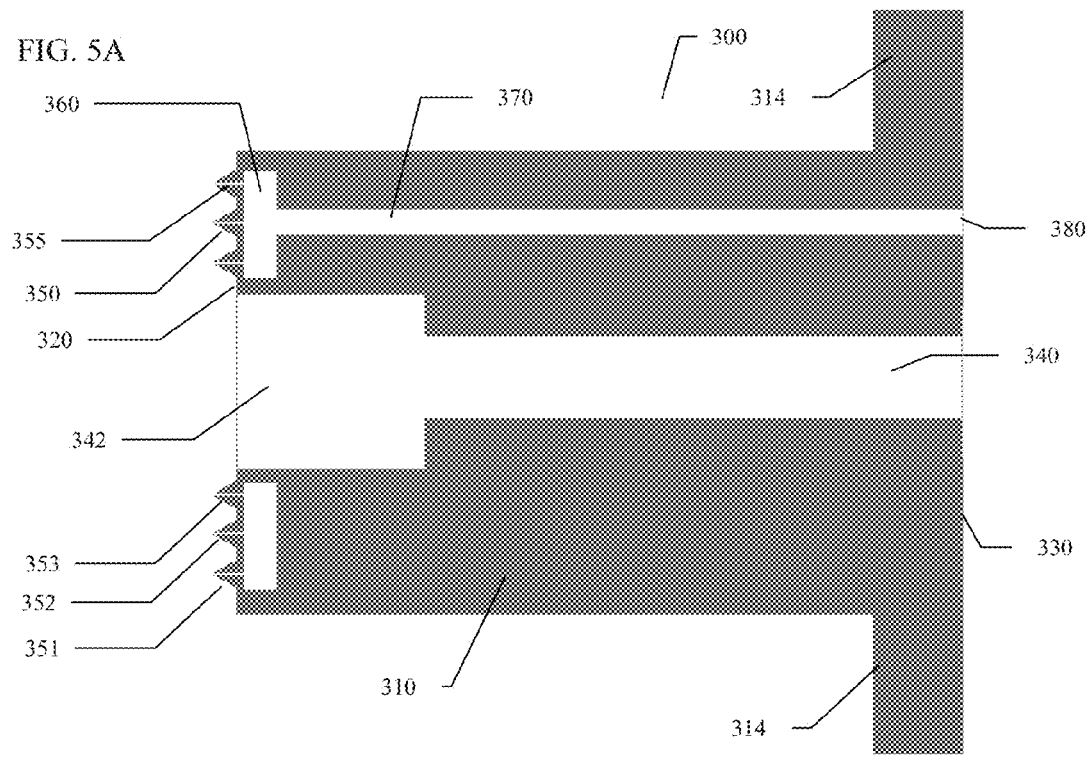
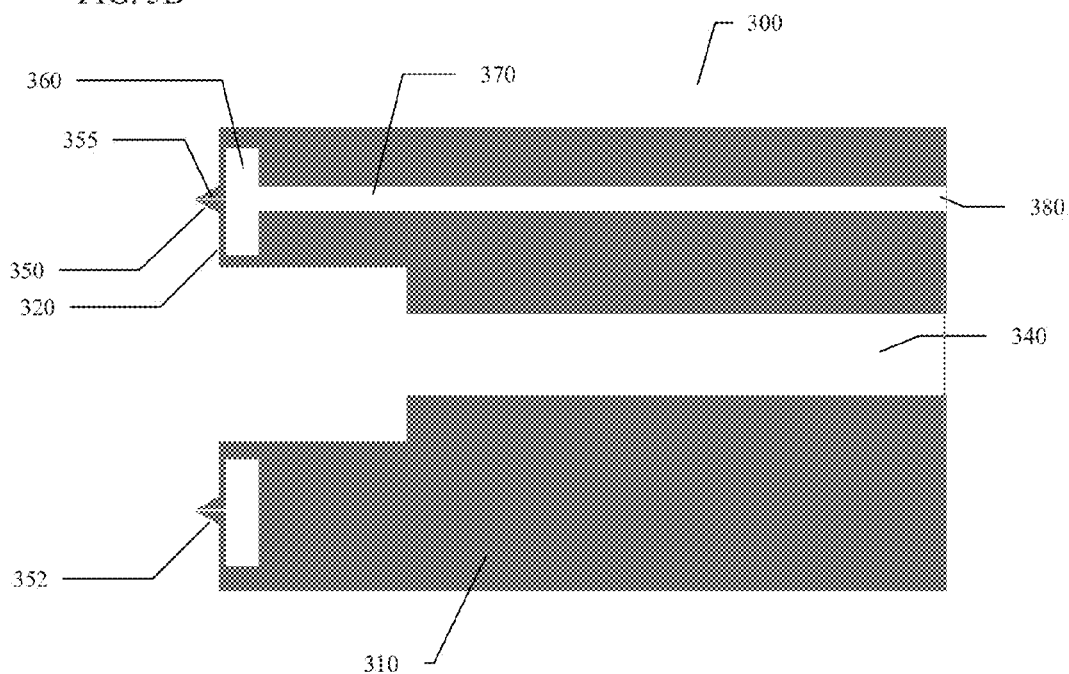

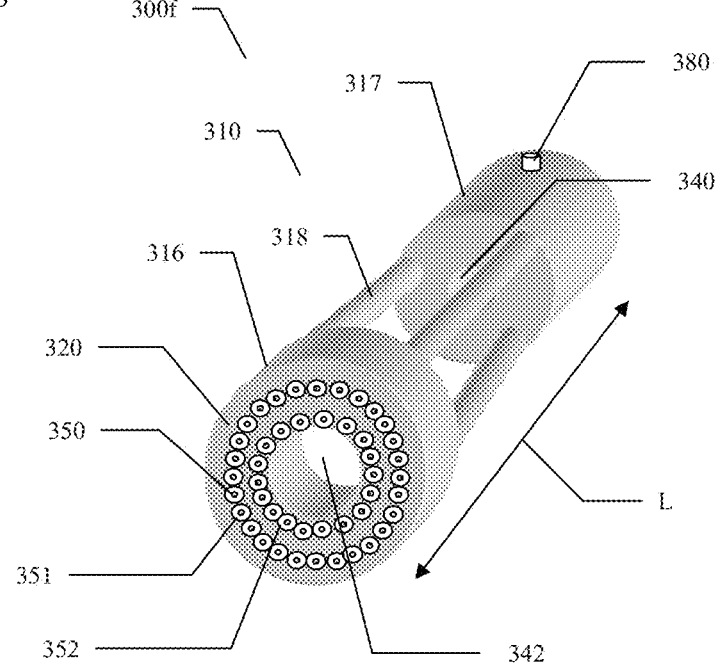

THERAPY DELIVERY DEVICE FOR ANASTOMOTIC JOINING OF TISSUE

FIELD OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site, especially when sealing an anastomosis between adjacent intestinal sections.

BACKGROUND OF THE INVENTION

Throughout the years the medical field has utilized various techniques in an effort to join or bond body tissue together. Historically, suturing was the accepted technique for rejoining severed tissues and closing wounds. Suturing was historically achieved with a surgical needle and a suturing thread, and more recently, with a variety of polymeric or metallic staples. The intended function of sutures is to hold the edges of a wound or tissue against one another during the healing process so as to reduce discomfort, pain, scarring and the time required for healing. Staples have recently been used to replace suturing when joining or anastomosing various body structures, such as, for example, the bowel. The surgical stapling devices employed to apply these staples are generally designed to simultaneously cut and seal an extended segment of tissue in a patient.

Linear or annular surgical stapling devices are employed by surgeons to sequentially or simultaneously apply one or more rows of surgical fasteners, e.g., staples or two-part fasteners, to body tissue for the purpose of joining segments of body tissue together and/or for the creation of an anastomosis. Linear surgical stapling devices generally include a pair of jaws or finger-like structures between which body tissue to be joined is placed. When the surgical stapling device is actuated and/or "fired," firing bars move longitudinally and contact staple drive members in one of the jaws, and surgical staples are pushed through the body tissue and into and against an anvil in the opposite jaw thereby crimping the staples closed. A knife blade may be provided to cut between the rows/lines of staples.

Annular surgical stapling devices generally include an annular staple cartridge assembly including a plurality of annular rows of staples (typically two or three), an anvil assembly operatively associated with the annular cartridge assembly, and an annular blade disposed internal of the rows of staples. In general, an end-to-end anastomosis stapler typically places an array or group of staples into the approximated sections of a patient's bowels or other tubular organs. The resulting anastomosis contains an inverted section of bowel which contains numerous "B" shaped staples to maintain a secure connection between the approximated sections of bowel.

Anastomotic leaks may result in significant morbidity and frequently death. In addition to the use of surgical staples, sealants, e.g., synthetic or biological sealants, can be applied to the surgical site to guard against leakage. The biological sealants are typically applied to the outer surface of the anastomosis using a dual lumen syringe or spray nozzle in a separate step. The delivery of the sealant can be compromised by an inability to get at or between individual staple sites, and along staple lines and tissue seams.

U.S. Patent Application No. 2013/0068819 entitled "Structure Containing Wound Treatment Material", discloses an anvil assembly for a circular stapling apparatus, where the anvil assembly includes an anvil head configured to support an anvil plate thereon; a shaft extending from the anvil head and configured to selectively engage a connection member of the circular stapling apparatus; an anvil plate operatively connected to the anvil head, the anvil plate defining a plurality of staple forming pockets therein; and a wound treatment material disposed in each staple forming pocket of the anvil plate. The wound treatment material is at least one of an adhesive, a sealant, a hemostat and a medicament.

U.S. Patent Applications Nos. 2011/0147432 and 2006/0108393, both entitled "Structure for applying sprayable wound treatment material", relate to surgical instruments, structures and methods for enhancing the properties of tissue to be repaired or joined and disclose a surgical stapling apparatus including a wound treatment material dispersion system for delivering wound treatment material to a target surgical site. The dispersion system includes an aperture formed in the anvil assembly oriented to dispense wound treatment material in an outward direction; and a source of wound treatment material in fluid communication with the aperture of the anvil assembly.

U.S. Patent Application No. 2011/0014181 entitled "Microneedle Delivery Device and Methods of Using Same" describes microneedle bioactive agent delivery systems, associated apparatus and methods of using such. The microneedles described are deliverable using a needle or syringe apparatus that can interface with existing medical devices or the devices can be used as standalone systems. The systems deliver at least one bioactive agent to a tissue in need thereof, for example, the myocardium.

U.S. Patent Application No. 2007/0038181 entitled "Method, system and device for delivering a substance to tissue" discloses devices and methods for delivering a substance to tissue or organs, particularly, the bladder, by a plurality of microneedles. The devices may include a delivery tube, a substance chamber to fill with the substance to be delivered, a plurality of needles, a plunger coupled to a handle movable relative to the tube to deliver the substance to the tissue through the needles, and a protective plate having at least one orifice therein, such that when the device is in a first, resting, position the needle tips are on a first side of the protective plate, and when the device is in a second, operational, position, the needles are on a second side of the protective plate.

U.S. Pat. No. 8,281,975, entitled "Surgical apparatus and structure for applying sprayable wound treatment material" discloses an apparatus for forming an anastomosis between adjacent sections of tissue. The apparatus includes a body portion; an actuation assembly operatively supported at a proximal end of the body portion; an anvil assembly movably mounted at the distal end of the body portion for movement toward and away from the body portion; an approximation assembly extending between the body portion and the anvil assembly for moving the anvil toward and away from the tubular body portion; a dispersion assembly operatively associated with the approximation assembly, the dispersion assembly including at least one angled surface defining at least one channel interposed between the anvil assembly and the body portion and being configured to dispense a fluid therefrom; and at least one conduit for conducting wound treatment material to the dispersion assembly.

U.S. Pat. No. 8,152,042 entitled "Annular Adhesive Structure" discloses an apparatus for sealing at the anastomotic site. In some embodiments, a washer or structural body is wrapped completely around an anvil shaft, with staples driven through the structural body to release the sealant.

U.S. Pat. No. 7,972,357 entitled "Extraluminal sealant applicator and method" and U.S. Pat. No. 7,744,624 disclose apparatus for applying sealant to a target tissue of a surgical site. The apparatus includes a handle, a conduit and an end effector. The handle has means configured and adapted for operating the end effector and dispensing biological sealant to the surgical site via the end effector. The conduit stores and/or carries sealant towards the end effector. The end effector is configured to clamp around a body organ or tissue and apply and confine biological sealant in a substantially uniform manner. More specifically, the references disclose a system for applying sealant to a target tissue of a surgical site, comprising: a two-part sealant comprising a first part and a second part; an apparatus comprising: a handle; an end effector in operative association with the handle, the end effector including a first jaw member, a second jaw member, and a sealant-applying structure configured for applying sealant to the target tissue; the first jaw member being in fluid communication with a first conduit and a second conduit to convey sealant to the sealant-applying structure; the second jaw member being in fluid communication with a third conduit and a fourth conduit to convey sealant to the sealant-applying structure; the first and third conduits configured for conveying the first part of the two-part sealant to the sealant-applying structure; and the second and fourth conduits configured for conveying the second part of the two-part sealant to the sealant-applying structure.

U.S. Pat. No. 8,096,458 entitled "Pouch used to deliver medication when ruptured" describes a surgical stapling device, comprising: a handle portion; an elongate body portion; and a head portion located at the distal end of the body portion, the head portion including an anvil assembly, a staple cartridge assembly and a knife blade, the staple cartridge assembly having an annular array or group of staples, the anvil assembly being connected to the body portion along a shaft, the anvil assembly including: an anvil plate defining a plurality of staple forming pockets therein and a recess; and a wound treatment material disposed substantially within the recess.

U.S. Pat. No. 8,241,308 entitled "Tissue fastening devices and processes that promote tissue adhesion" discloses a fastener for fastening tissue segments having tissue surfaces, the fastener comprising: a first fastener member defining a fluid opening configured to receive a therapeutic agent, a plurality of fluid ports configured to deliver the therapeutic agent to the tissue segments, and a passageway between the fluid opening and the plurality of fluid ports; and a second fastener member having a substantially flat base and a post extending from the base proximate a center of the base, the post defining an opening for receiving and retaining the first fastener member such that the tissue segments to be fastened are retained between the first and second fastening members, the substantially flat base extending radially beyond a periphery of the post; wherein a longitudinal axis extends through the fluid opening, the fluid ports being radially arranged about the axis.

Post-operative leakage of the anastomotic seals has been shown to lead to morbidity and mortality. A number of technologies are related to direct application of material to the serosal layer after stapling by either dripping or spraying. The problems associated with this technique are that access is very difficult and it is challenging to assess whether or not the material was applied to the right spot and completely around the anastomosis. The material is also applied on top of the serosal layer when the target site is actually subserosal along the staple line. Applying a therapeutic agent to the serosal layer of the colon requires the material to migrate through the serosa and to the staple region, then provide a biological affect, and overcome the problems associated with a leak formation, all within 24-48 hours, assuming the material was applied to the correct spot intraoperatively. One of the most challenging steps in the application of a topical adjunctive therapy to a colorectal anastomosis is to provide the material to the site because of the extreme limitation in access to the site. Some colorectal anastomoses are performed relatively "low" in a patient (i.e. lower anterior resection) and the actual staple line is deep within the pelvic canal, which makes a topical application of material around the circumference very difficult. Other technologies attempt to deliver the materials upon deploying of the stapler, resulting in complex equipment which delivers materials into highly compressed tissue.

SUMMARY OF THE INVENTION

The present invention relates to surgical instruments and methods for enhancing properties of tissue repaired or joined by surgical staples and, more particularly to surgical instruments and methods designed to apply a therapeutic material to enhance the properties of repaired or adjoined tissue at a target surgical site, especially when sealing an anastomosis between adjacent intestinal sections so as to improve tissue viability and to prevent leakage.

The present invention, in one embodiment, relates to a circular anastomosis stapler kit that delivers a therapeutic agent followed by stapling of tissue. The kit contains a device having a stapling head with an extending shaft and an anvil. The anvil can be removably connected to the shaft and a delivery head for delivering a therapeutic agent into the tissue. The delivery head has a cylindrical-shaped body with a front side and an opposing rear side, a central cylindrical opening therethrough that slidably moves over the shaft, a channel within the ring-shaped body terminating in a port opening on the front side and a plurality of circumferentially positioned hollow microneedles disposed on the front side surface of the ring-shaped body that are in fluid communication with the channel. The port opening can be connected to a pressurized therapeutic agent delivery system, wherein the pressurized therapeutic agent delivery system can include a syringe. The delivery head can have at least 10 hollow microneedles that are from 50 microns to about 1000 microns in diameter and from about 100 microns to about 2000 microns long. The delivery head can further include a plurality of circumferentially positioned hollow microneedles that are disposed on the rear side and in fluid communication with the channel. The front side of the delivery head can face a proximal lumen of the tissue, while the rear side would face a distal lumen of the tissue. The delivery head can be composed of two half-ring hollow bodies that are joined together by a joining means, such as a hinge, a plurality of pins or a plurality of magnetic strips. The therapeutic agent can be a drug, an enzyme, a growth factor, a peptide, a protein, a nutrient, an excipient, a cell, or combinations thereof.

The present invention, in another embodiment, relates to method for performing anastomosis by sliding the delivery head described above onto the shaft, bringing the microneedles in contract with the tissue, delivering the therapeutic agent into the tissue through the microneedles, removing the delivery head from the shaft, and stapling the tissue. The time elapsed after the step of delivering the therapeutic agent into the tissue until starting the step of stapling the tissue is preferably at least 20 seconds. The therapeutic agent is preferably injected into a non-compressed tissue.

The present invention, in another embodiment, relates to a method for performing anastomosis by positioning a stapling head of a stapler in a proximal tissue lumen and positioning an anvil of the stapler in a distal tissue lumen; slidably positioning a first delivery head on a shaft extending from the stapling head with a front side of the first delivery head facing the proximal tissue lumen and slidably positioning a second delivery head on a shaft or anvil pin connected to an anvil with a front side of the second delivery head facing the distal tissue lumen; sliding the first delivery head towards the stapling head, until the microneedles pierce the proximal tissue lumen; expressing a therapeutic agent from a first syringe connected to the port on the first delivery head causing the therapeutic agent flow through the channel and through the microneedle channels into tissue of the proximal tissue lumen; concurrently or sequentially with the two preceding steps, sliding the second delivery head towards the anvil until the microneedles pierce the distal tissue lumen; expressing the therapeutic agent from a second syringe connected to the port on the second delivery head causing the therapeutic agent flow through the channel and through the microneedle channels into tissue of the distal tissue lumen; removing the delivery head from the shaft; and connecting the stapler head to the anvil and performing stapling of the proximal and the distal tissue lumen with the stapler. The delivery head comprises a ring-shaped body having a centering cylindrical opening and at least one channel through the body that terminates in a port opening; a plurality of circumferentially positioned hollow microneedles disposed on the front side having microneedle channels in fluid communication with the channel. The delivery head preferably has at least 10 hollow microneedles that are from 50 microns to about 1000 microns in diameter and from about 100 microns to about 2000 microns long. The therapeutic agent is preferably a drug, an enzyme, a growth factor, a peptide, a protein, a nutrient, an excipient, a cell, or combinations thereof.

The present invention, in another embodiment, relates to a method for performing anastomosis by positioning a stapling head of a stapler in a proximal tissue lumen and positioning an anvil of the stapler in a distal tissue lumen; slidably positioning a delivery head comprising a ring-shaped body having a centering cylindrical opening on a shaft extending from the stapling head and connected to the anvil; approximating the stapling head and the anvil until the microneedles pierce the proximal and the distal tissue lumen; expressing a therapeutic agent from a syringe connected to the port causing the therapeutic agent flow through the channel and through the microneedle channels into tissue of the proximal and the distal tissue lumens; removing the delivery head from the shaft; and stapling the proximal and the distal tissue lumen with the stapler. The delivery head has a channel within the body terminating in a port opening, a plurality of circumferentially positioned hollow microneedles that are disposed on a front side of the delivery head facing the stapling head and on an opposing rear side of the delivery head facing the anvil that are in fluid communication with the channel. The delivery head preferably has at least 10 hollow microneedles that are from 50 microns to about 1000 microns in diameter and from about 100 microns to about 2000 microns long. The delivery head can be composed of two half-ring hollow bodies that are joined together by a joining means, such as a hinge, a plurality of pins, or a plurality of magnetic strips. The therapeutic agent can be a drug, an enzyme, a growth factor, a peptide, a protein, a nutrient, an excipient, a cell, or combinations thereof.

BRIEF DESCRIPTION OF THE FIGURES

FIGS. 5A and 5B show schematic longitudinal cross-sectional views of embodiments of the delivery head of the present invention.

FIG. 8 shows schematic prospective view of an embodiment of the delivery head of the present invention.

DETAILED DESCRIPTION OF THE INVENTION

Colorectal surgery often involves the resection of a segment of the colon and rectum. Following a colorectal resection, the colon and rectum are drawn together with a circular stapler or handsewn, and an end-to-end anastomosis is performed. Post-op leakage of the anastomosis has been shown to lead to morbidity and mortality.

Figure 1A:
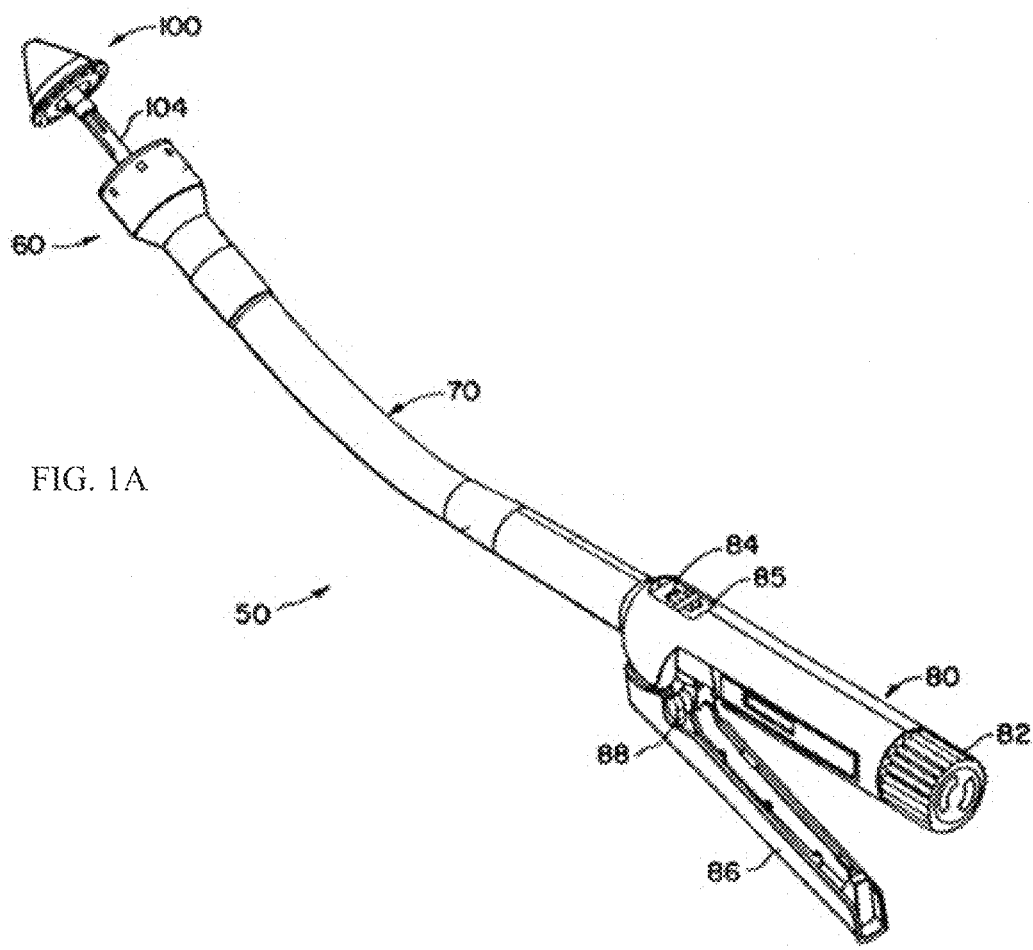
FIGS. 1A, 1B and 1C show prospective view and schematic cross-sectional views of a surgical anastomosis stapling instrument or stapling device for performing a circular anastomosis stapling operation.

Referring now to FIG. 1A, a generic surgical anastomosis stapling instrument or stapling device for performing a circular anastomosis stapling operation is shown, with the figure taken from the U.S. Pat. No. 5,271,544 "Surgical anastomosis stapling instrument", assigned to Ethicon, Inc., Somerville, N.J., and incorporated herein by reference in its entirety for all purposes. Various modifications and iterations of the shown stapling device are known in the art, having similar features. The circular anastomosis surgical stapling instrument 50 includes a distal stapling head assembly 60 connected by a longitudinally curved support shaft assembly 70 to a proximal actuator handle assembly 80. The stapling instrument includes an anvil assembly or anvil 100 which is slidable longitudinally relative to the stapling head assembly 60 and mounted on an axially extending moveable shaft 104. An optional rotatable adjusting knob 82 is provided at the proximal end of the actuator handle assembly 80 for adjusting the spacing between the stapling head assembly 60 and the anvil assembly 100. An optional movable indicator 84 is visible through an optional window 85 on top of the handle assembly 80 to indicate the staple height selected by rotation of the adjusting knob 82. The indicator 84 is movable indicating that the anvil gap is within a desired operating range of the stapling instrument 50. The position of the indicator 84 also indicates whether the selected staple height is large or small.

A staple actuating lever 86 is pivotally mounted on the actuator handle assembly 80 for driving the surgical staples from the stapling head assembly 60 when the anvil assembly 100 is closed to provide the desired staple height. A pivotal latching member 88 is mounted on the handle assembly 80 for locking the staple actuating lever 86 against movement to preclude actuation of the stapling head assembly 60 when the anvil gap is outside of a predetermined range.

Figure 1B:
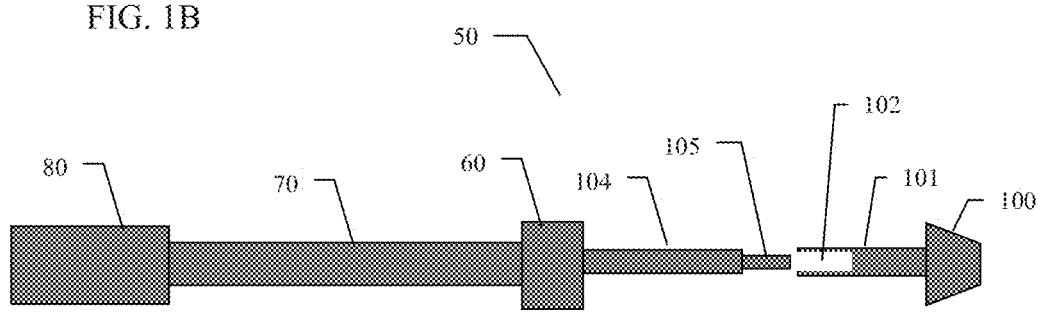

In a typical design of circular anastomosis surgical stapling instrument 50, as schematically shown in FIG. 1B, anvil 100 can be connected in a lockable way to axially extending moveable shaft 104 extending from stapling head 60. Anvil 100 connection to shaft 104 is typically established via anvil pin 101, locking for instance through engagement of a shaft 104 tip 105 into a sleeve 102 formed in anvil pin 101. Other ways of engaging and locking anvil 100 to shaft 104 are known, but all involve lockable engagement of anvil pin 101 to shaft 104.

Figure 1C:
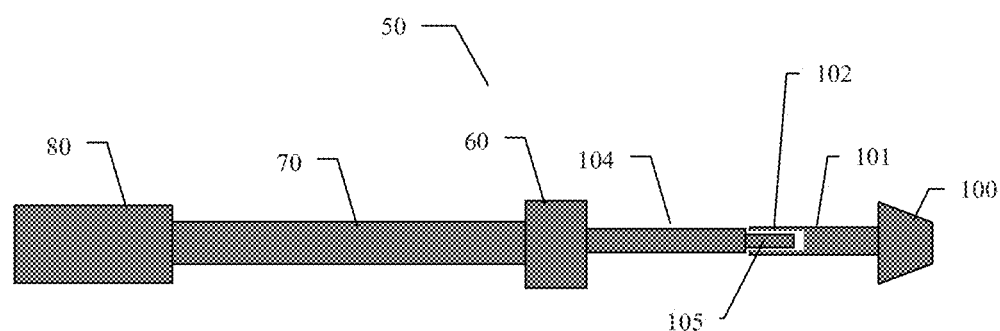

Referring now to FIG. 1C, anvil 100 is shown lockably connected to shaft 104 through engagement of tip 105 into a sleeve 102 while FIG. 1B is illustrating anvil 100 not connected to shaft 104.

The anastomosis can be performed by a variety of techniques known in the art. In one exemplary technique, low anastomosis of colon to rectum using the anastomotic stapler is performed. Briefly, after stapler 50 is inserted through the anus, the descending colon is fixated around anvil 100, with purse string sutures tied around the shaft and the rectal stump is fixated around stapling head 60 with purse string sutures also tied around the shaft. Anvil 100 is then pulled towards stapling head 60 and then the staples are deployed to join the tissue of the descending colon and rectal stump at their respective serosal surfaces, with simultaneous action of circular scalpel (not shown) within stapler 50 cutting away excessive tissue (inverted bowel) closest to shaft, resulting in anastomosis. Stapler 50 is then removed.

According to the present invention, application of therapeutic material refers to subserosal injection into the tissue, prior to the joining of the tissue by staples. The device of the present invention delivers therapeutic agents to the subserosa of the large intestines at the anastomotic site prior to performing the anastomosis. Therapeutic material or therapeutic agent refers to any medically useful substance or combination of substances, which can improve tissue viability, including drugs, enzymes, growth factors, peptides, proteins, nutrients, excipients, and any other injectable pharmaceutical agents. Examples of therapeutic agents are also autologous cells and fibrinogen.

The delivery head of the present invention allows for direct subserosal delivery of therapeutic agents to the regions which have not yet been stapled. The delivery of therapeutic agents is performed beneath the serosa layer on both the anvil and stapling head side prior to staple deployment. Introducing the therapeutic agents before stapling overcomes the problem of accessibility and improves the surgeon's ability to provide complete (360 degree) coverage around the anastomotic joint. The application of therapeutic material to the staple interface region prior to stapling can still be supplemented with a topical application of agents to the serosal layer after stapling if desired.

Clinical evidence shows the formation of a full wall intestinal defect at or near the anastomotic site may occur as soon as 1-2 days post-op, with typical time period when the clinical symptoms of leaks occur being from 1 to 5 days post-op. See, for example, K. Jönsson, H. Jiborn, B. Zederfeldt, "Breaking strength of small intestinal anastomoses", The American Journal of Surgery, v. 145, pp. 800-803, 1983; Y.-H. Ho, M. A. T. Ashour, "Techniques for colorectal anastomosis", World Journal of Gastroenterology, 16(13), pp. 1610-1621, 2010.

Figure 2A:
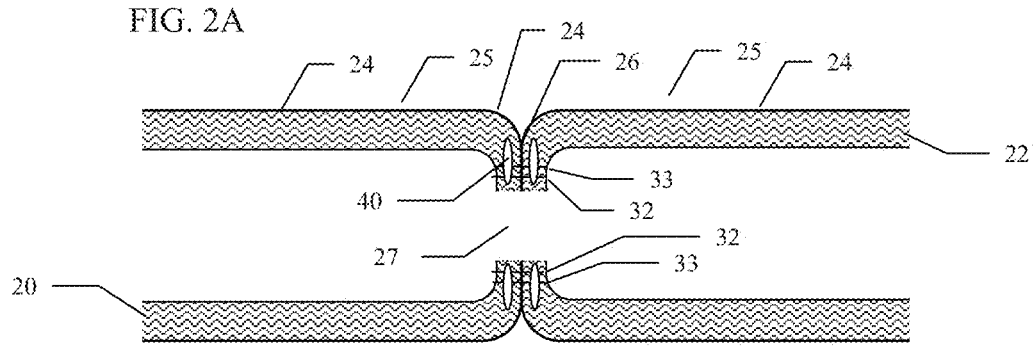
FIGS. 2A and 2B show schematic cross-sectional side views of anastomotic joints of tubular lumens.
Figure 2B:
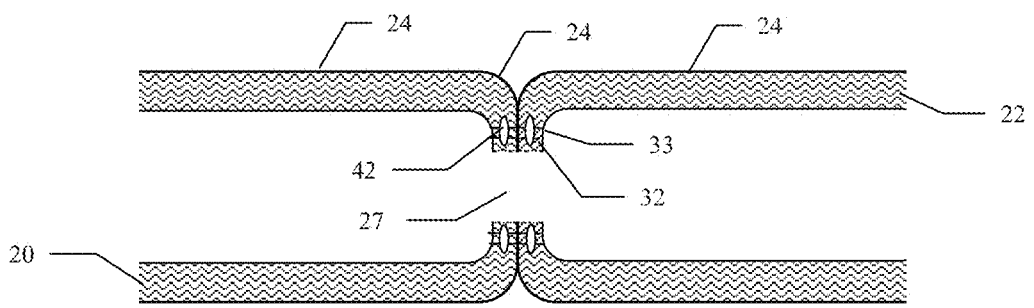
Figure 2C:
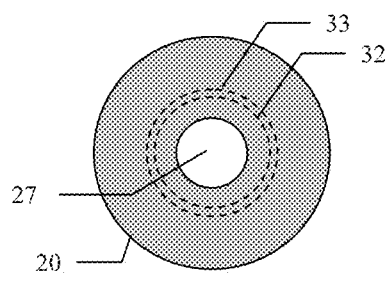
FIGS. 2C, 2D, 2E, 2F and 2G show additional cross-sectional frontal views of anastomotic joints.

Referring now to FIGS. 2A and 2B, anastomotic joint 26 of tubular proximal lumen 20 and distal lumen 22 is schematically presented in a longitudinal cross-section, with rows of staples 32 and 33 arranged in concentric circles around anastomosis opening 27 as shown in FIG. 2C in a cross-sectional frontal view. Proximal lumen 20 and distal lumen 22 are joined at serosal (external) surfaces 24.

Figure 2D:
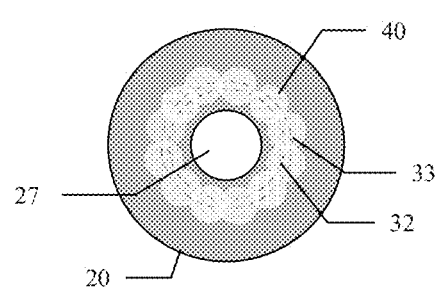

According to one embodiment of the present invention, the targeted sub-serosal areas for the delivery of therapeutic agents are shown schematically as delivery zones 40 (FIG. 2A), continuously covering areas immediately around and between staples 32 and 33 and extending from close to anastomosis opening 27 to beyond larger diameter staple row 33 and towards tubular sections 25 of proximal lumen 20 and distal lumen 22. Delivery zones 40 are further shown in FIG. 2D and are targeting all subserosal area of tissue of proximal lumen 20 and distal lumen 22 (not shown in FIG. 2D) which are forming anastomotic joint 26.

Figure 2E:
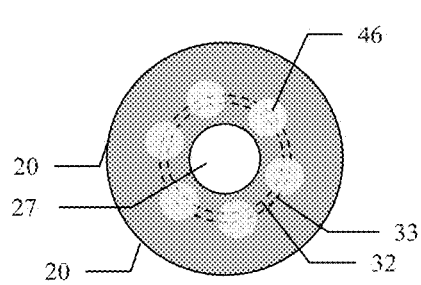
Figure 2F:
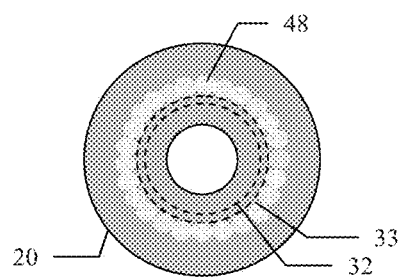
Figure 2G:
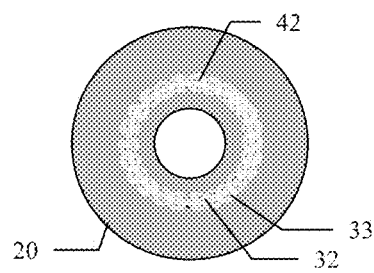

In another embodiment of the present invention, targeted sub-serosal areas for the delivery of therapeutic agents are shown schematically as delivery zones 42 shown in FIG. 2B covering areas only immediately around and between staples 32 and 33, further shown in FIG. 2G and targeting subserosal area of tissue of proximal lumen 20 and distal lumen 22 (not shown in FIG. 2G) immediately around and between staple rows 32 and 33.

In yet another embodiment of the present invention, targeted sub-serosal areas for the delivery of therapeutic agents are shown schematically as intermittent delivery zones 46 shown in FIG. 2E covering intermittent areas immediately around and between staples 32 and 33 and extending from close to anastomosis opening 27 to beyond larger diameter staple row 33.

In still another embodiment of the present invention, targeted sub-serosal areas for the delivery of therapeutic agents are shown schematically as delivery zones 48 shown in FIG. 2F covering areas only beyond larger staples row 33.

It is apparent from the above description that in various embodiments of the present invention delivery zones of the therapeutic agent into subserosal areas are contemplated around and between staples and also beyond rows of staples, generally into tissues which are in contact with other tissues in the anastomotic joint and into tissues which are subject to formation of ulcerations and tissue necrosis within and around anastomotic joint.

Delivery heads of the present invention are designed to deliver therapeutic agents into subserosal delivery zones, as described above, immediately before the formation of anastomotic joint.

Figure 3:
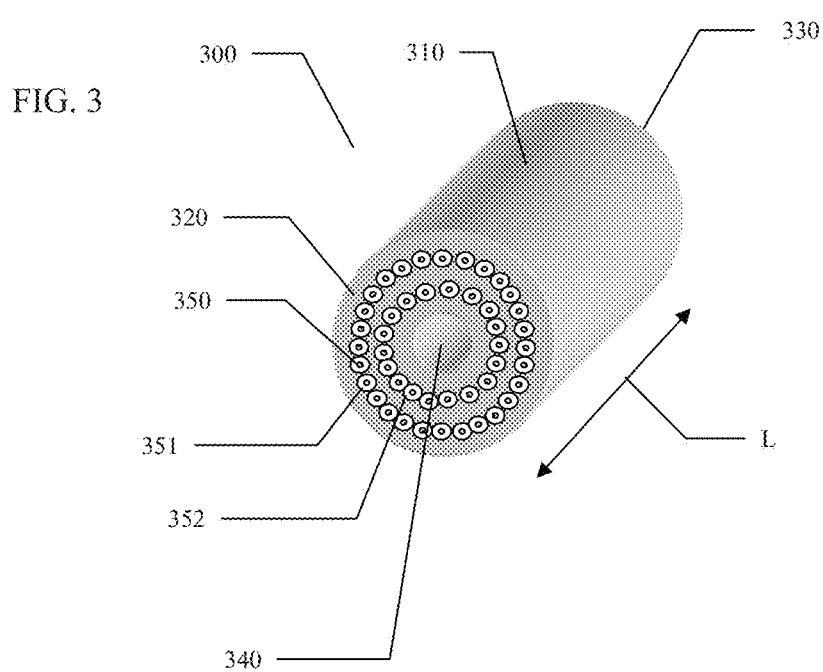
FIG. 3 shows schematic prospective view of an embodiment of the delivery head of the present invention.

Referring now to FIG. 3, one embodiment of delivery head 300 of the present invention is schematically presented as comprising an elongated generally ring-shaped or cylindrical body 310 having front side 320 and rear side 330, with an array or group of microneedles 350 disposed on front side 320 around centering cylindrical opening 340 having diameter matching, but larger than the external diameter of anvil pin 101 and/or shaft 104 so that anvil pin 101 and/or shaft 104 can slidably enter centering cylindrical opening 340. Centering cylindrical opening 340 serves as centering aperture for positioning delivery head 300 onto anvil pin 101 and/or onto shaft 104 and for sliding delivery head 300 on anvil pin 101 and/or on shaft 104. Microneedles 350, in one embodiment, are arranged in two concentric array or groups 351 and 352 around centering cylindrical opening 340. Length L of delivery head 300 is from about 5 mm to about 250 mm, more preferably from 20 mm to about 100 mm. Microneedles 350, in other embodiments, can be arranged around centering cylindrical opening 340 in various configurations, including random, concentric with one, two, three, or more concentric array or groups, checkered array, spiral array, or any other configuration, all assuring complete and uniform coverage of front side 320 with microneedles 350.

Figure 4A:
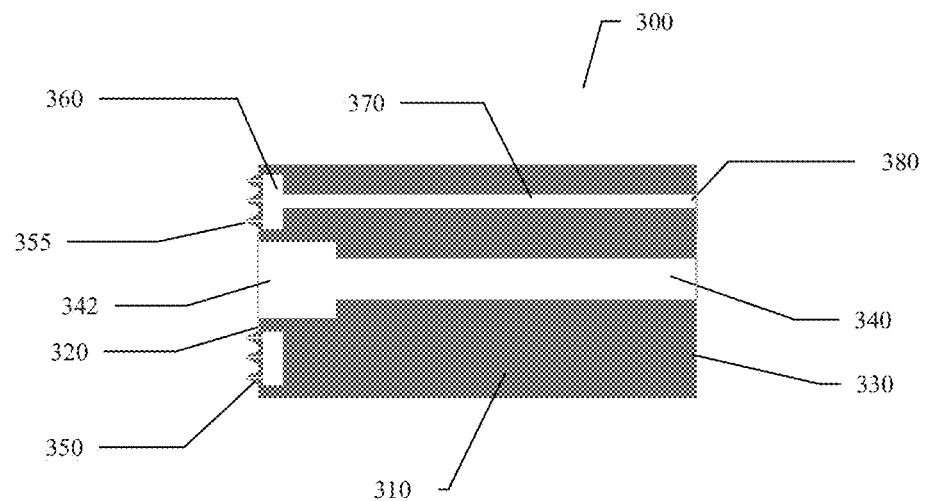
FIGS. 4A and 4B show schematic cross-sectional views of embodiments of the delivery head of the present invention.
Figure 4B:
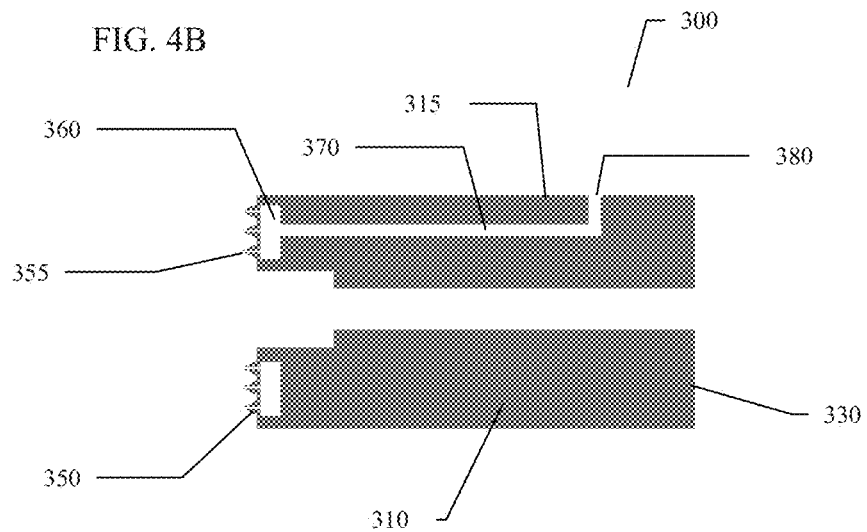

Referring now to FIGS. 4A and 4B, a cross-sectional view of the embodiment of device 300 shown in FIG. 3 is presented, with hollow microneedles 350 arranged in three concentric rows and having microneedle channels 355 through the whole length of microneedle 350 and connecting microneedles 350 to compartment 360 positioned inside body 310 in proximity to front side 320. Compartment 360 is, in one embodiment, a ring-shaped chamber situated under surface of front side 320; compartment 360 is in fluid communication with all microneedles 350. Compartment 360 is connected to port 380 via channel 370. Port 380 is shown situated on rear side 330, but is can be also positioned on side wall 315 of body 310 as shown in FIG. 4B. Port 380 is used to connect a cannula (not shown) to deliver therapeutic agents into compartment 360 and from compartment 360 into microneedle channels 355 within hollow microneedles 350 and from microneedles 350 into tissue (not shown). Centering cylindrical opening 340 optionally has a cavity 342 having an increased diameter open to front side 320. The depth of optional cavity 342 is from about 3 mm to about 75 mm as measured from front side 320, preferably from 5 mm to 30 mm. The diameter of optional cavity 342 is at least 20% larger than the external diameter of anvil pin 101 and/or shaft 104. In one embodiment, the diameter of optional cavity 342 is approximately equal to or smaller than the diameter of anastomosis opening 27. In one embodiment, the diameter of optional cavity 342 is approximately equal to or smaller than the smaller diameter staple row 32 as shown in the series of FIG. 2.

Referring now to FIG. 5A, a cross-sectional view of an embodiment of device 300 shown in FIG. 4 is presented, with array or group of hollow microneedles 350 having microneedle channels 355 in three concentric rows 351, 352, 353. Other arrangements of microneedles 350 into an array or group are contemplated, such as checkered arrangement (not shown). The microneedles can be also distributed in an uneven arrangement as single or partial rings or shapes. Optional flange-shaped handles 314 are disposed on rear side 330 to facilitate manual handling of delivery head 300.

Referring now to FIG. 5B, a cross-sectional view of an embodiment of device 300 is presented, with array or group of hollow microneedles 350 having microneedle channels 355 comprising only one circular array or group comprising one row 352 of microneedles 350.

Figure 5C:
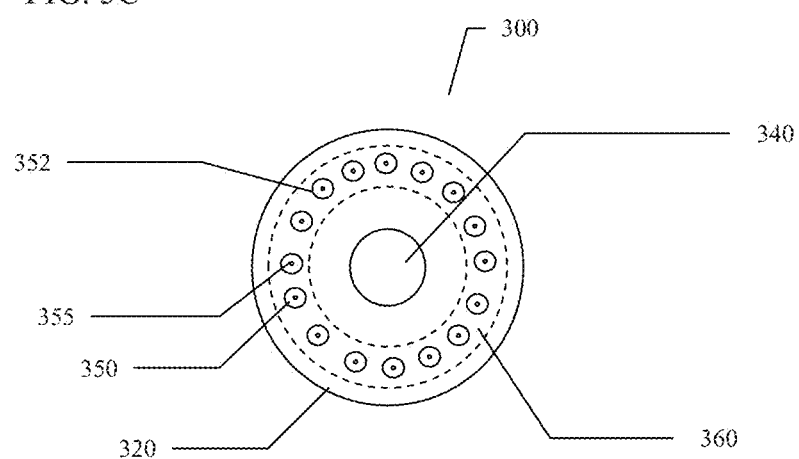
FIG. 5C shows an additional frontal view of an embodiment of the present invention.

Referring now to FIG. 5C, a view of front side 320 of device 300 is shown, corresponding to embodiment of FIG. 5B, having array or group of hollow microneedles 350 having microneedle channels 355 comprising only one circular array or group comprising one row 352 of microneedles 350. Compartment 360 is shown by dashed lines as being situated below surface of front side 320 and in fluid communication with microneedle channels 355.

Figure 6A:
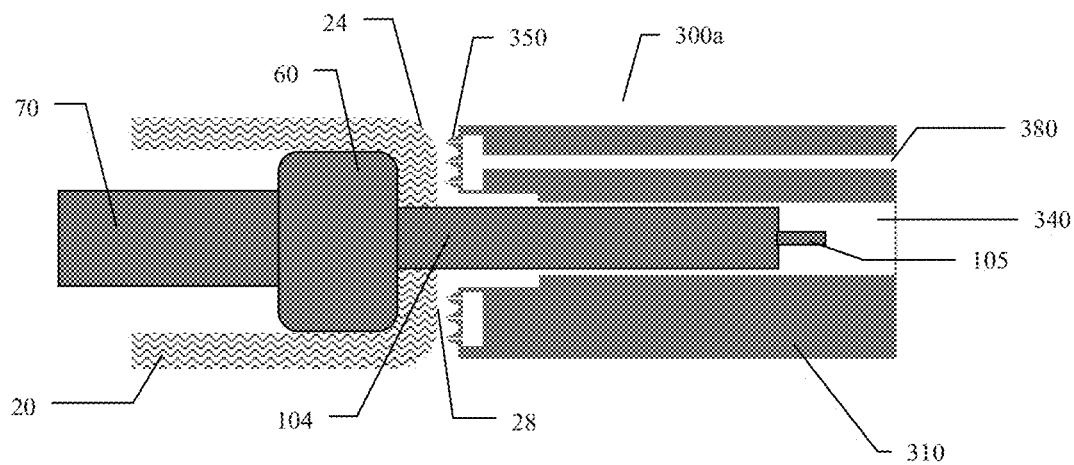
FIGS. 6A, 6B, 6C, 6D, 6E and 6F show schematic longitudinal cross-sectional views of embodiments of the present invention in operation during anastomosis using the anastomotic stapler.

Referring now to FIG. 6A, in preparation for use, after stapling head 60 was installed in the proximal lumen 20 and prior to deploying staples forming anastomotic joint, delivery head 300a is fitted over shaft 104 with shaft 104 slidably entering centering cylindrical opening 340. Shaft 104 is used as a guide to advance delivery head 300a towards tissue areas 28 of proximal lumen 20 which are about to be joined by stapling in forming anastomotic joint, with microneedles 350 facing towards tissue areas 28.

Figure 6B:
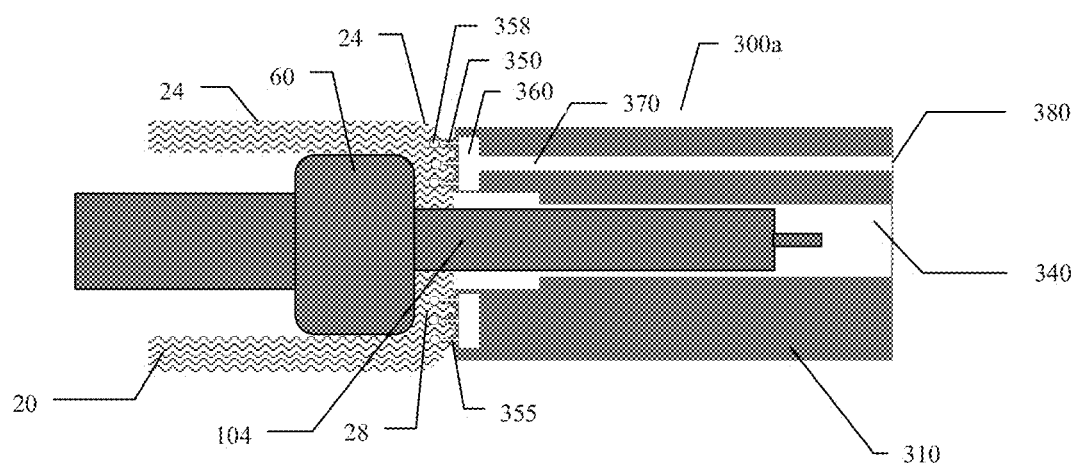

Referring now to FIG. 6B, delivery head 300a is shown further slidably advanced over shaft 104 and is pushed against stapling head 60 with microneedles 350 piercing serosal surface 24 and entering subserosal tissue of tissue areas 28. Therapeutic agent is then injected into channel 370 through port 380 using any suitable injection device, such as syringe (not shown); therapeutic agent advances into compartment 360 and into microneedle channels 355 within microneedles 350, with therapeutic agent entering subserosal tissue of tissue areas 28. Injected therapeutic agent can form microdroplets 358 in the vicinity of microneedles 350 within tissue areas 28. Therapeutic agent can then at least partially disperse or dissipate within subserosal tissue of tissue areas 28 immediately prior to deploying staples forming anastomotic joint. In one embodiment, therapeutic agent is pre-injected into channel 370 through port 380, thus pre-filling compartment 360 prior to microneedles 350 piercing serosal surface 24 and entering subserosal tissue of tissue areas 28, in which case the air inside channel 370 and compartment 360 is removed prior to microneedles 350 entering tissue.

Figure 6C:
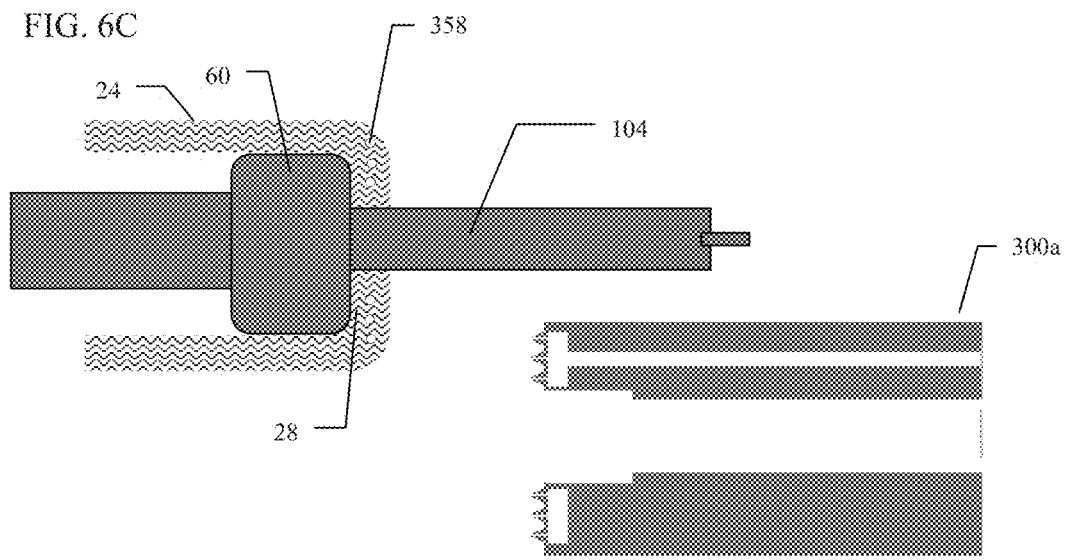

Referring now to FIG. 6C, after the delivery of therapeutic agent, delivery head 300a is removed from shaft 104, leaving microdroplets 358 of therapeutic agent in subserosal tissue areas 28.

Figure 6D:
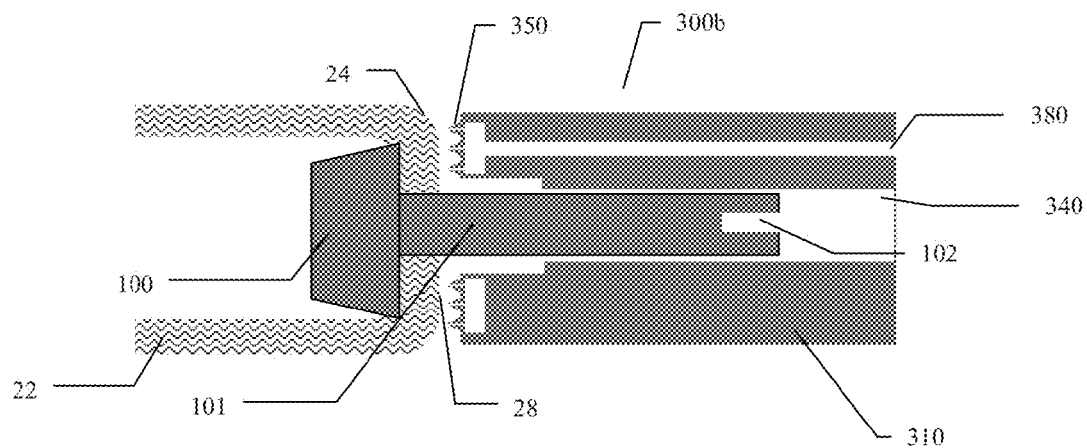

In a similar fashion, and referring now to FIG. 6D, in preparation for use, after anvil 100 was installed in the distal lumen 22 and prior to deploying staples forming anastomotic joint, delivery head 300b, having substantially similar design to delivery head 300a, is fitted over anvil pin 101, with anvil pin 101 slidably entering centering cylindrical opening 340. Anvil pin 101 is used as a guide to advance delivery head 300b towards tissue areas 28 of distal lumen 22 which are about to be joined by stapling in forming anastomotic joint, with microneedles 350 facing towards tissue areas 28.

Figure 6E:
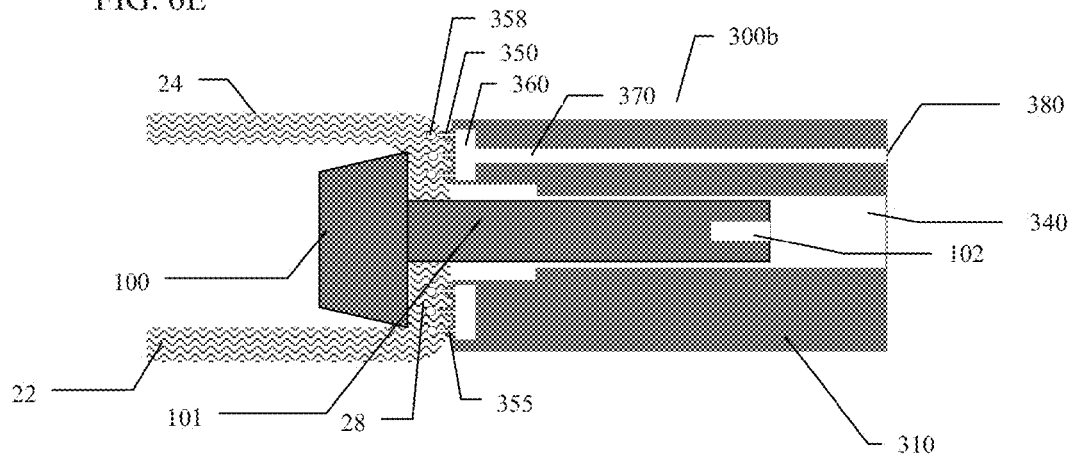

Referring now to FIG. 6E, delivery head 300b is further slidably advanced over anvil pin 101 and is pushed against anvil 100 with microneedles 350 piercing serosal surface 24 and entering subserosal tissue of tissue areas 28. Therapeutic agent is then injected into channel 370 through port 380 using any suitable injection device, such as syringe (not shown); therapeutic agent advances into compartment 360 and into microneedle channels 355 within microneedles 350, with therapeutic agent entering subserosal tissue of tissue areas 28. Injected therapeutic agent can form microdroplets 358 in the vicinity of microneedles 350 within tissue areas 28. Therapeutic agent can then at least partially disperse or dissipate within subserosal tissue of tissue areas 28 immediately prior to deploying staples forming anastomotic joint.

Figure 6F:
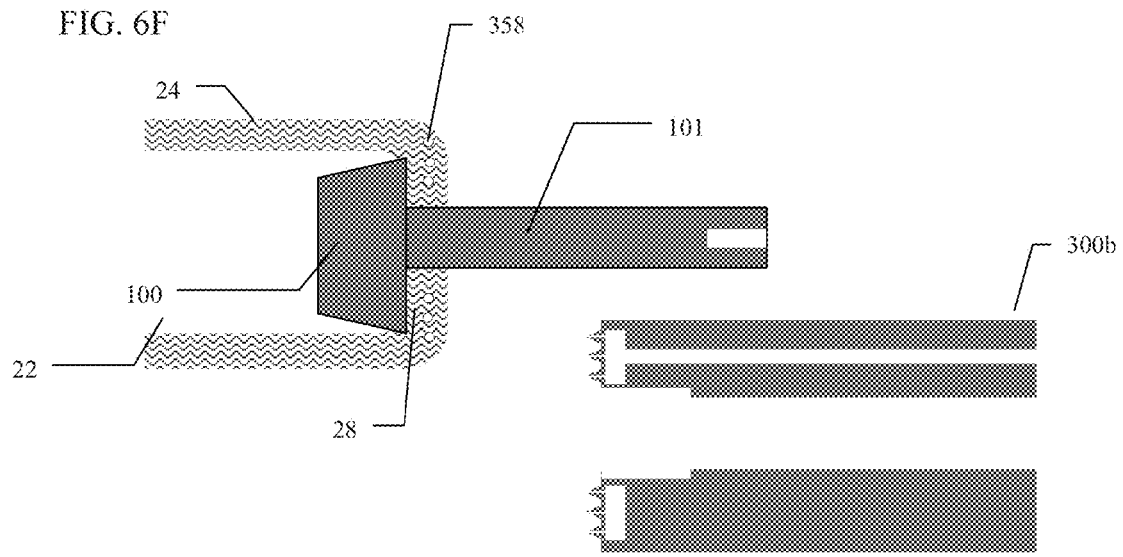

Referring now to FIG. 6F, after the delivery of therapeutic agent, delivery head 300b is removed from anvil pin 101, leaving microdroplets 358 of therapeutic agent inside tissue areas 28.

After the delivery of the therapeutic agent, and removal of delivery heads 300a and 300b from anvil pin 101 and shaft 104, anvil pin is lockably connected to shaft 104 through engagement of tip 105 into sleeve 102 as shown in FIGS. 1B and 1C, and anastomotic stapling is performed as usual by deploying staples from the circular anastomosis surgical stapling instrument. Advantageously, tissue areas forming anastomotic joint have been treated with therapeutic agent, improving tissue viability and preventing ulceration and tissue necrosis.

Figure 7A:
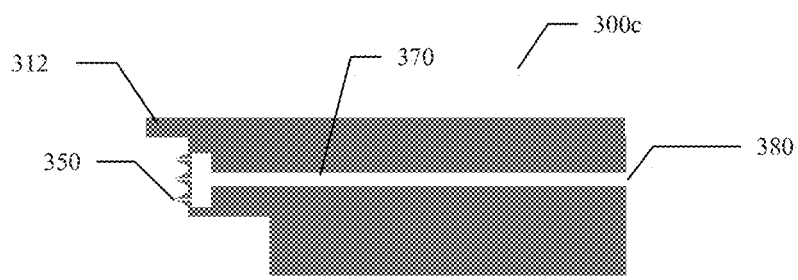
FIGS. 7A, 7B and 7C show schematic cross-sectional side views of embodiments of the delivery head of the present invention.
Figure 7B:
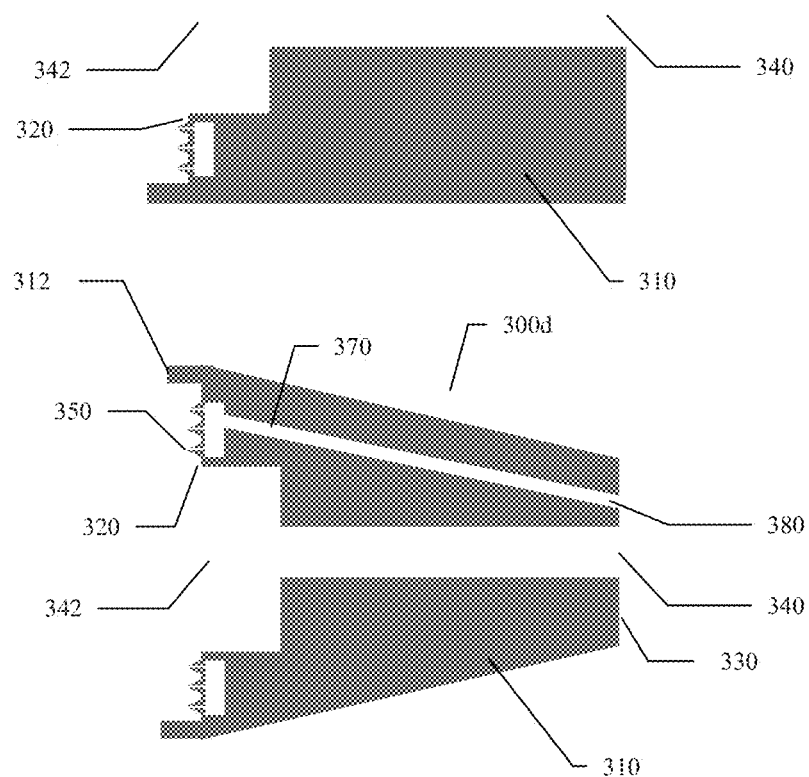
Figure 7C:
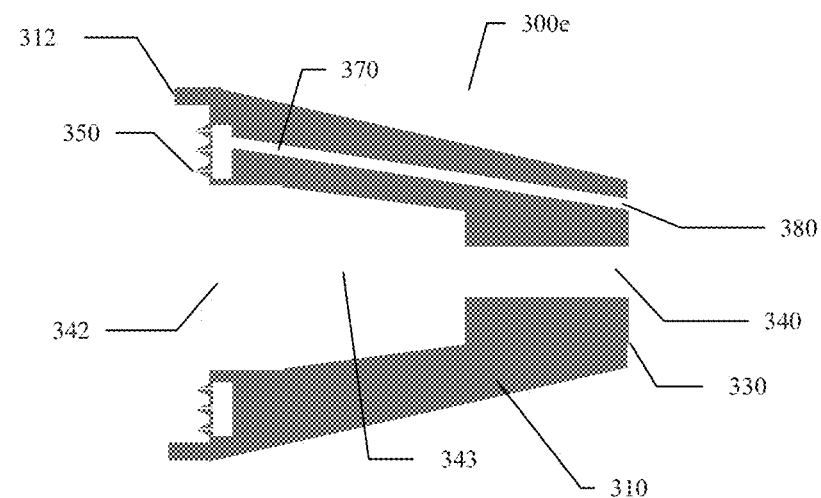

Referring now to FIGS. 7A-7C, additional embodiments of delivery head 300 are presented in a schematic cross-sectional view. FIG. 7A shows an embodiment of delivery head 300c having a circumferential lip 312 comprising a raised ridge around the outside circumference of front side 320. Optional lip 312 is adapted to surround proximal or distal lumen positioned on anvil or on stapling head.

FIG. 7B shows an embodiment of delivery head 300d whereby body 310 has generally a conical shape with diameter of rear side 330 smaller that is less than the diameter of front side 320, such as 20%, 40%, or 70% smaller, preferably 50% smaller.

FIG. 7C shows an embodiment of delivery head 300e whereby body 310 has generally a conical shape similar to the embodiment of FIG. 7B, further having a conical shaped cutout 343 between centering cylindrical opening 340 and a second area 343 having an increased diameter relative to opening 340.

Referring now to FIG. 8, it is shown an embodiment of delivery head 300f, whereby body 310 comprises a ring-shaped housing 316 connected by a plurality of supports 318 to an axially aligned centering ring 317. Delivery head 300f preferably has at least two supports 318 between housing 316 and centering ring 317, more preferably three or four supports 318 are used, with three supports 318 shown in FIG. 8. Ring-shaped housing 316 has hollow microneedles 350 disposed on front side 320, optionally arranged in several arrays or groups such as arrays 351 and 352. Opening 342 in the ring of ring-shaped housing 316 is an area defined by having a diameter that is at least 20% larger than the external diameter of anvil pin 101 and/or shaft 104 (neither shown in FIG. 8). Ring-shaped housing 316 has internal compartment 360 (not shown in FIG. 8) in fluid communication with hollow microneedles 350 and with channel 370 (not shown in FIG. 8) inside at least one of supports 318 and within at least a portion of centering ring 317. Channel 370 (not shown in FIG. 8) terminates in port 380 adapted for connecting to a pressurized source of therapeutic agent, such as a syringe (not shown in FIG. 8). Centering ring 317 has centering cylindrical opening 340 adapted for centering delivery head 300f on anvil pin 101 and/or on shaft 104. In one embodiment, length L of delivery head 300f is at least equal to the length of anvil pin 101 and/or on shaft 104, in another embodiment length L is from 10% to 100% longer than anvil pin 101 and/or shaft 104. In all embodiments, length L is selected so as to ensure that once delivery head 300f is positioned onto anvil pin 101 and/or onto shaft 104 and slidably advanced towards tissue areas 28, anvil pin 101 and/or shaft 104 are situated within centering ring 317 for reliable centering.

Figure 9A:
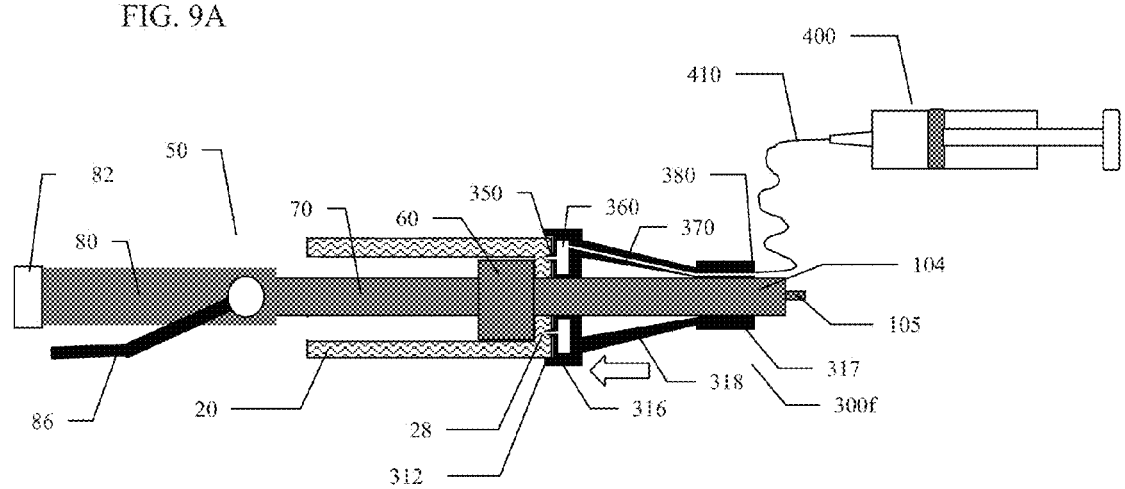
FIGS. 9A and 9B show schematic cross-sectional side views of embodiments of the present invention in operation during anastomosis using the anastomotic stapler.
Figure 9B:
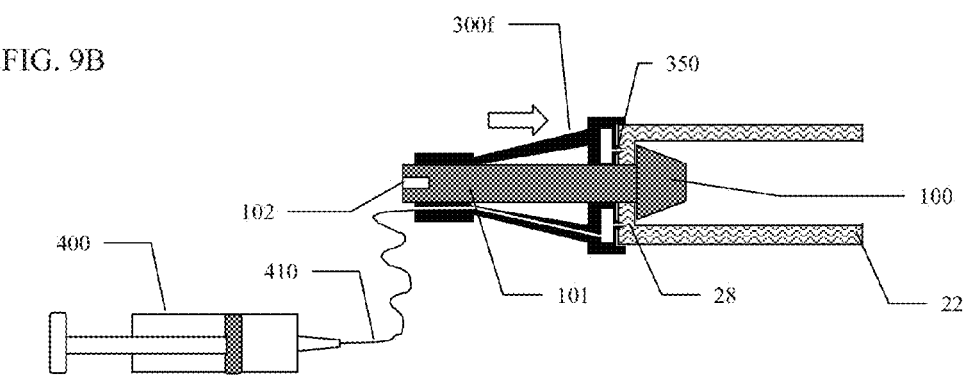

Referring now to FIGS. 9A and 9B, embodiments of delivery heads 300f are shown in operation in conjunction with circular anastomosis surgical stapling instrument 50. Arrows indicate the direction of advancing delivery heads 300f on anvil pin 101 (FIG. 9B) and on shaft 104 (FIG. 9A) towards tissue areas 28 on proximal lumen 20 and distal lumen 22 until microneedles 350 contact and pierce tissue areas 28. Syringes 400 are shown connected to ports 380 via cannulas 410 enabling therapeutic agent (not shown) to be expressed from syringes 400 through cannulas 410 into ports 380 and further via channel 370 into compartment 360 and through hollow microneedles 350 into tissue areas 28. After the delivery of therapeutic agent into tissue areas 28, delivery heads 300f are removed and shaft 104 is connected to anvil pin 101 and the stapling is performed.

According to embodiments of the present invention, hollow microneedles 350 are from 50 microns to about 1500 microns in diameter, more preferably 100 to 1000 microns, such as 200 or 500 microns. Microneedle channels 355 are from about 25 microns to about 500 microns, more preferably 50 to 300 microns, such as 100 microns. According to embodiments of the present invention, hollow microneedles 350 are from 100 microns to about 2000 microns long, such as 500 microns or 1000 microns long. In certain embodiments, there are from about 10 to about 500 or 1000 microneedles on front side of the delivery head, more preferably at least 20 microneedles, most preferably at least 50 or 100 microneedles arranged in one or several microneedle arrays or groups.

According to one embodiment of the present invention, injection volume is about 0.1-2 ml per injection, more preferably 0.2-0.5 ml per injection.

According to embodiments of the present invention, diameter of delivery heads of the present invention is selected to fit into surgical anastomosis stapling instrument, and is ranging from about 100 mm to about 30 mm, more preferably from 15 mm to 28 mm, such as 21 mm, 24 mm, or 26 mm. The diameter of centering cylindrical opening 340 is from about 4 mm to about 10 mm, such as 5, 6, or 7 mm.

Optional lip 312 extends from surface of front side 320 to lip height from about 1 mm to about 8 mm, preferably 2 mm to 5 mm, such as 4 mm.

Figure 10A:
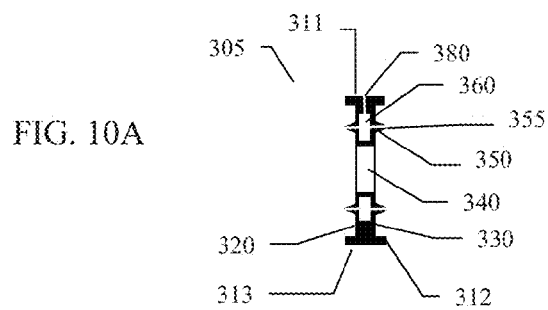
FIGS. 10A, 10B, 10C, 10D, 10E, 10F, and 10G show schematic cross-sectional side views and prospective views of alternative embodiments of the present invention and the embodiments in operation during anastomosis using the anastomotic stapler.
Figure 10B:
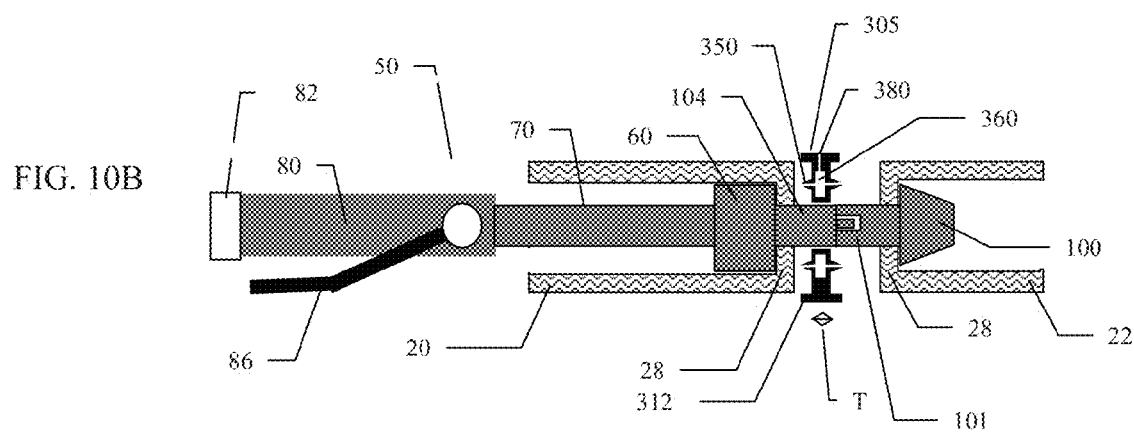

Referring now to FIGS. 10A and 10B, an embodiment of the present invention is presented in a schematic cross-sectional view. As shown in FIG. 10A, delivery head 305 comprises a cylindrical or ring-shaped hollow body 311 having front side 320 and opposing rear side 330, and sidewall 313 with ring opening comprising centering cylindrical opening 340 and having optional lip 312. A plurality of microneedles 350 are disposed on both front side 320 and rear side 330, and compartment 360 is disposed inside the hollow body 311. Microneedle channels 355 are in fluid communication with compartment 360 which is in turn in fluid communication with port 380. Thickness T of delivery head 305 is from about 2 mm to about 10 mm, such a 6 mm.

Figure 10C:
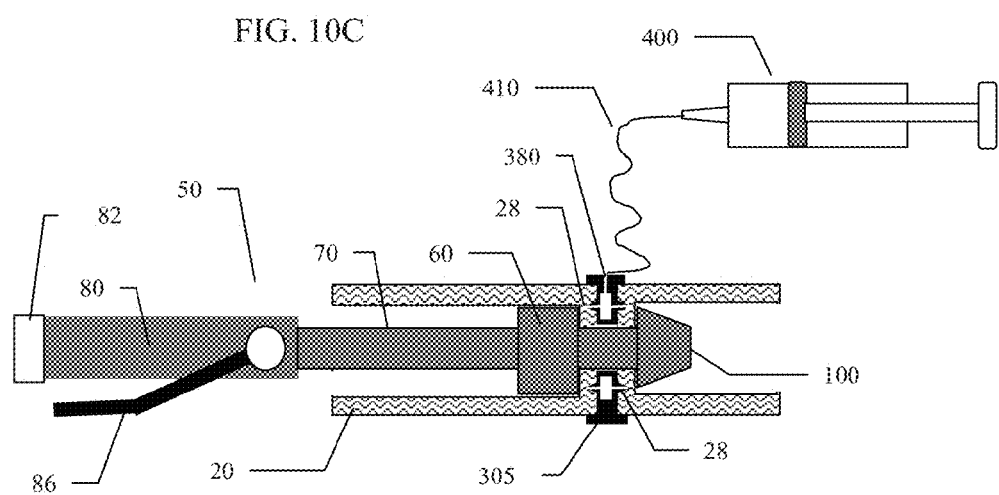

As shown in a schematic cross-sectional view in FIG. 10B, in use, delivery head 305 is positioned on either shaft 104 or anvil pin 101 after which shaft 104 and anvil pin 101 are engaged. Prior to positioning delivery head 305 onto shaft 104 or anvil pin 101, or after positioning, syringe 400 containing therapeutic agent is connected to port 380 via cannula 410. Anvil 100 is then approximated to stapling head 60 by turning knob 82 resulting in delivery head 305 squeezed between anvil 100 and stapling head 60 resulting in microneedles 350 on both front side 320 and rear side 330 piercing tissue and entering tissue areas 28, as shown in FIG. 10C. Therapeutic agent is then expressed from syringe 400 and advances via cannula 410 into port 380 and then into compartment 360 and into microneedle channels and is injected into tissue areas 28. After the injection is performed, the anvil pin is disengaged from shaft 104, and delivery head 305 is removed. Anvil pin is then re-engaged with shaft 104 and the stapling is performed.

Figure 10D:
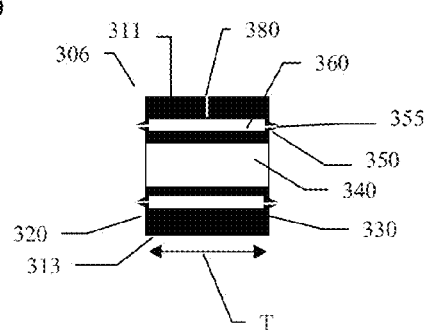
Figure 10F:
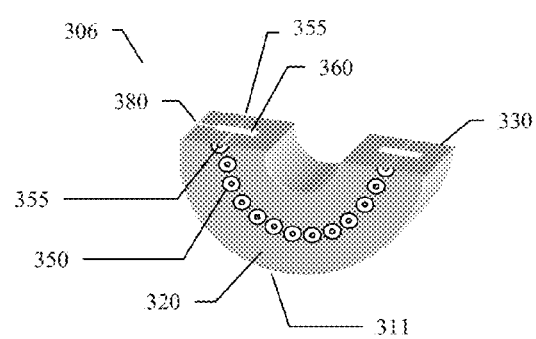
Figure 10E:
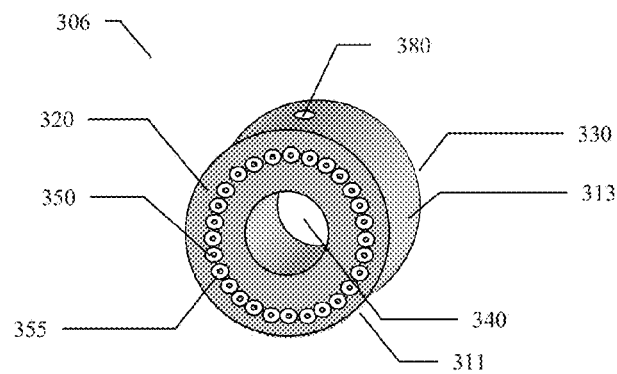

Referring now to FIG. 10D, an embodiment of the present invention is presented in a schematic cross-sectional side view. Also referring to FIGS. 10E and 10F, the same embodiment is shown in a schematic prospective view and in a schematic prospective cross-sectional view respectively. In the view shown in FIG. 10F, compartment 360 is shown in hollow body 311. Delivery head 306 has a substantially similar construction to delivery head 305 shown in FIGS. 10A-C, with the difference being the ring thickness T of ring shaped delivery head 306 being larger compared to thickness of delivery head 305. Thickness T of ring shaped delivery head 306 device is from 10 mm to 20 mm, such as 15 mm.

Figure 10G:
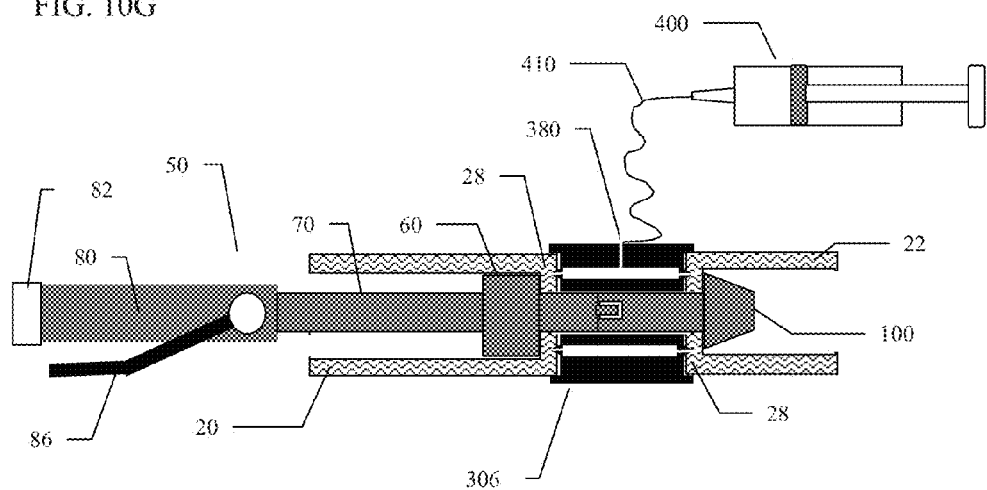

Referring now to FIG. 10G, as shown in a schematic cross-sectional view, in use, delivery head 306 is engaged with syringe 400 and anastomosis surgical stapling instrument 50 in a similar fashion to the earlier shown embodiment of FIG. 10C.

Figure 11A:
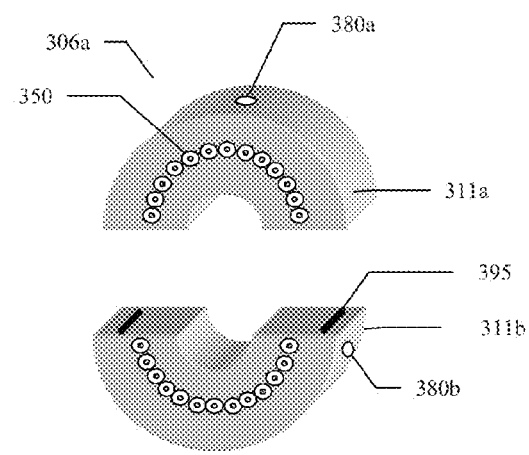
FIGS. 11A, 11B, and 11C show schematic prospective views of alternative embodiments of the present invention.
Figure 11B:
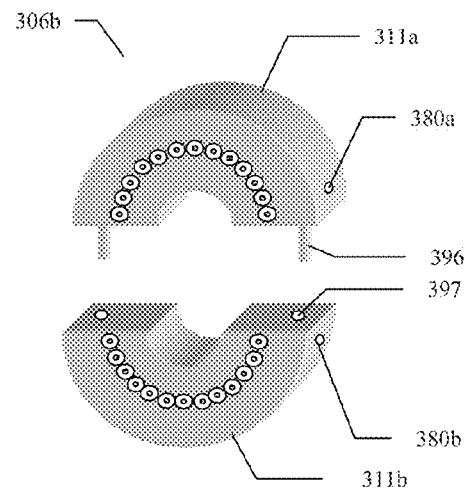
Figure 11C:
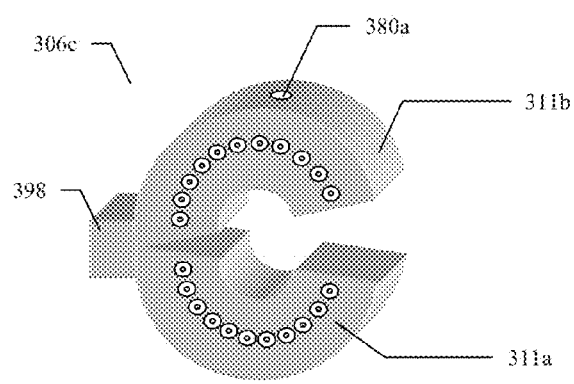

Referring now to FIGS. 11A, 11B and 11C, further alternative embodiments of the present invention are presented in schematic prospective views. As shown in FIG. 11A, embodiment of delivery head 306a having generally a similar design to device 306 of FIG. 10, comprises half-ring hollow bodies 311a and 311b which when joined together via magnetic strips 395 (only visible on half-ring hollow body 311b) form delivery head 306a having ring shape similar to device 306 of FIG. 10. Delivery head 306a can be positioned onto shaft 104 connected to anvil pin 101 and also removed from shaft 104 connected to anvil pin 101 by separately positioning and removing hollow bodies 311a and 311b. Thus delivery head 306a can be assembled from hollow bodies 311a and 311b directly on shaft 104 connected to anvil pin 101 and can also be removed from shaft 104 connected to anvil pin 101 by separately removing hollow bodies 311a and 311b. Both hollow bodies 311a and 311b have ports 380a and 380b for delivery of therapeutic agent through ports 380a and 380b.

As shown in FIG. 11B, another embodiment of delivery head 306b having generally a similar design to device 306a, comprises half-ring hollow bodies 311a and 311b which when joined together via pins 396 entering matching apertures 397 form delivery head 306b having ring shape similar to device 306 of FIG. 10. Thus delivery head 306b can be assembled from hollow bodies 311a and 311b directly on shaft 104 connected to anvil pin 101 and can also be removed from shaft 104 connected to anvil pin 101 by separately removing hollow bodies 311a and 311b. Both hollow bodies 311a and 311b have ports 380a and 380b for delivery of therapeutic agent through ports 380a and 380b. Optionally, in an alternative embodiment, only one port 380a is used and the therapeutic agent, after entering hollow body 311a through port 380a, can transfer into hollow body 311b via one or more pins 396 which in this embodiment are hollow pins having channels inside. Port 380b is not used in this case.

As shown in FIG. 11C, in another embodiment, delivery head 306c having generally a similar design to device 306a, comprises half-ring hollow bodies 311a and 311b which are joined at hinge 398. Hollow bodies 311a and 311b form delivery head 306c which can open and close around shaft 104 connected to anvil pin 101 in a clam-shell like fashion, opening and closing at hinge 398. Thus delivery head 306c can be positioned directly on shaft 104 connected to anvil pin 101 and can also be removed from shaft 104 connected to anvil pin 101 by opening and closing delivery head 306c in a clam-shell like fashion at hinge 398.

Advantageously, and as can also be seen from FIGS. 6, 9, 10B, 10C, 10G, the delivery of therapeutic agent is performed prior to deploying staples, i.e. into non-compressed tissue, or under low compression of tissue. Low compression of tissue is defined as tissue being compressed less relative to the compression of tissue under deployment of staples. Thus therapeutic agent can potentially penetrate the tissue and is expected not to be pushed from the tissue due to high compressive forces. Advantageously, therapeutic agent is delivered into both proximal and distal lumens of tissue.

Advantageously, because therapeutic agent delivery is performed prior to and independently of staples deployment, more area of the tissue is available for delivering the agent, as microneedles do not interfere with staples and larger density of needles is possible. Areas of tissue that are about to be penetrated by staples can also be treated. Thus tissue can be treated with higher uniformity and with a higher density of injections of therapeutic agent using the microneedles of the present invention. In certain embodiments, there are from 10 to 500 microneedles on front side of the delivery head, more preferably at least 20 microneedles, most preferably at least 50 microneedles arranged in one or several microneedle arrays. An equal number of microneedles can be disposed on the rear side of embodiments shown in FIGS. 10 and 11.

Advantageously, because therapeutic agent delivery is performed prior to staples deployment, therapeutic agent can potentially redistribute in the tissue more uniformly during the time period between the delivery of the therapeutic agent and deployment of staples. The time period from therapeutic agent delivery through microneedles to the deployment of staples is from about 10 seconds to about 10 minutes, more preferably from about 20 seconds to about 3 minutes, most preferably 1 to 2 minutes.

While the invention has been described above with reference to specific embodiments thereof, it is apparent that many changes, modifications, and variations can be made without departing from the inventive concept disclosed herein. Accordingly, it is intended to embrace all such changes, modifications, and variations that fall within the spirit and broad scope of the appended claims. All patent applications, patents, and other publications cited herein are incorporated by reference in their entirety.

We claim:

1. A circular anastomosis stapler kit that delivers a therapeutic agent followed by stapling of tissue comprising:
    a) a stapling head with a shaft extending from said stapling head and an anvil, wherein the anvil can be removably connected to the shaft; and
    b) a delivery head for delivering a therapeutic agent into the tissue, said delivery head comprising:
        a. a ring-shaped body having a front side and an opposing rear side and having a central cylindrical opening therethrough that slidably moves over the shaft;
        b. a channel within the ring-shaped body terminating in a port opening; and
        c. a plurality of circumferentially positioned hollow microneedles disposed on the front side surface of the ring-shaped body that are in fluid communication with the channel.

2. The stapler of claim 1, wherein the port is connectable to a pressurized therapeutic agent delivery system.

3. The stapler of claim 2, wherein the pressurized therapeutic agent delivery system comprises a syringe.

4. The stapler of claim 1, wherein said delivery head comprises at least 10 hollow microneedles and wherein said hollow microneedles are from 50 microns to about 1000 microns in diameter and from about 100 microns to about 1000 microns long.

5. The stapler of claim 1, wherein said delivery head further comprises a plurality of circumferentially positioned hollow microneedles disposed on the rear side, the microneedles having microneedle channels in fluid communication with the channel.

6. The stapler of claim 5, wherein the front side of the delivery head faces a proximal lumen of the tissue and the rear side faces a distal lumen of the tissue.

7. The stapler of claim 5, wherein said comprises two half-ring hollow bodies joined together.

8. The stapler of claim 7, wherein half ring hollow bodies are joined together with a hinge, a plurality of pins, or a plurality of magnetic strips.

9. The stapler of claim 1, wherein said therapeutic agent is a drug, an enzyme, a growth factor, a peptide, a protein, a nutrient, an excipient, a cell, or combinations thereof.

10. A method for performing anastomosis comprising:
a. sliding onto a shaft of a stapling head with the shaft extending from said stapling head and an anvil, said delivery head comprising: 1) a ring-shaped body having a front side and an opposing rear side and having a central cylindrical opening therethrough that slidably moves over the shaft; 2) a channel within the ring-shaped body terminating in a port opening; and 3) a plurality of circumferentially positioned hollow microneedles disposed on the front side surface of the ring-shaped body that are in fluid communication with the channel;
b. bringing the microneedles in contract with the tissue;
c. delivering the therapeutic agent into the tissue through the microneedles;
d. removing the delivery head from the shaft; and
e. stapling the tissue.

11. The method of claim 10, wherein time elapsed after the step of delivering the therapeutic agent into the tissue until starting the step of stapling the tissue is at least 20 seconds.

12. The method of claim 10, wherein the therapeutic agent is injected into a non-compressed tissue.

13. A method for performing anastomosis comprising:
a) positioning a stapling head of a stapler in a proximal tissue lumen and positioning an anvil of the stapler in a distal tissue lumen;
b) slidably positioning a first delivery head on a shaft extending from the stapling head with a front side of the first delivery head facing the proximal tissue lumen and slidably positioning a second delivery head on a shaft connected to an anvil with a front side of the second delivery head facing the distal tissue lumen;
wherein the delivery head comprises
a ring-shaped body having a centering cylindrical opening and at least one channel through the body that terminates in a port opening;
a plurality of circumferentially positioned hollow microneedles disposed on the front side having microneedle channels in fluid communication with the channel;
c) sliding the first delivery head towards the stapling head, until the microneedles pierce the proximal tissue lumen;
d) expressing a therapeutic agent from a first syringe connected to the port on the first delivery head causing the therapeutic agent flow through the channel and through the microneedle channels into tissue of the proximal tissue lumen;
e) concurrently or sequentially with the steps c) and d), sliding the second delivery head towards the anvil until the microneedles pierce the distal tissue lumen; expressing the therapeutic agent from a second syringe connected to the port on the second delivery head causing the therapeutic agent flow through the channel and through the microneedle channels into tissue of the distal tissue lumen;
f) removing the delivery heads from the shaft;
g) connecting the stapler head to the shaft and performing stapling of the proximal and the distal tissue lumen with the stapler.

14. The method of claim 13, wherein said delivery head comprises at least 10 hollow microneedles and wherein said hollow microneedles are from 50 microns to about 1000 microns in diameter and from about 100 microns to about 1000 microns long.

15. The method of claim 13, wherein said therapeutic agent is a drug, an enzyme, a growth factor, a peptide, a protein, a nutrient, an excipient, a cell, or combinations thereof.

16. A method for performing anastomosis comprising:
a) positioning a stapling head of a stapler in a proximal tissue lumen and positioning an anvil of the stapler in a distal tissue lumen;
b) slidably positioning a delivery head comprising a ring-shaped body having a centering cylindrical opening on a shaft extending from the stapling head and connected to the anvil;
the delivery head having a channel within the body terminating in a port opening;
the delivery head having a plurality of circumferentially positioned hollow microneedles disposed on a front side of the delivery head facing the stapling head and on an opposing rear side of the delivery head facing the anvil, with the microneedles having microneedle channels in fluid communication with the channel;
c) approximating the stapling head and the anvil until the microneedles pierce the proximal and the distal tissue lumen;
d) expressing a therapeutic agent from a syringe connected to the port causing the therapeutic agent flow through the channel and through the microneedle channels into tissue of the proximal and the distal tissue lumens;
e) removing the delivery head from the shaft;
f) stapling the proximal and the distal tissue lumen with the stapler.

17. The method of claim 16, wherein said delivery head comprises at least 10 hollow microneedles and wherein said hollow microneedles are from 50 microns to about 1000 microns in diameter and from about 100 microns to about 1000 microns long.

18. The method of claim 16, wherein said delivery head comprises two half-ring hollow bodies joined together.

19. The method of claim 18, wherein said half-ring hollow bodies are joined together with a hinge, a plurality of pins, or a plurality of magnetic strips.

20. The method of claim 16, wherein said therapeutic agent is a drug, an enzyme, a growth factor, a peptide, a protein, a nutrient, an excipient, a cell, or combinations thereof.

* * * * *